US007973215B2

(12) United States Patent
Kuo

(10) Patent No.: US 7,973,215 B2
(45) Date of Patent: Jul. 5, 2011

(54) METHOD FOR THE INTRODUCTION OF A HETEROLOGOUS POLYNUCLEOTIDE INTO A MUSHROOM

(75) Inventor: Chun-Yi Kuo, Taipei County (TW)

(73) Assignee: Mycomagic Biotechnology Co., Ltd., Taipei County (TW)

( * ) Notice: Subject to any disclaimer, the term of this patent is extended or adjusted under 35 U.S.C. 154(b) by 248 days.

(21) Appl. No.: 12/101,799

(22) Filed: Apr. 11, 2008

(65) Prior Publication Data

US 2009/0260102 A1      Oct. 15, 2009

(51) Int. Cl.
*C12N 15/82*  (2006.01)
*C12N 15/87*  (2006.01)

(52) U.S. Cl. ........................................ 800/292

(58) Field of Classification Search .................. 800/278, 800/292; 435/252.3, 468, 470, 471, 476
See application file for complete search history.

(56) References Cited

U.S. PATENT DOCUMENTS

2004/0072325 A1*   4/2004   Anazawa et al.  ..........  435/252.3

FOREIGN PATENT DOCUMENTS

WO      95/02691      1/1995
WO      98/45455      10/1998

OTHER PUBLICATIONS

C. Burns et al.; Efficient GFP expression in the mushrooms *Agaricus bisporus* and *Coprinus cinereus* requires introns; Journal; 2005; pp. 191-199; vol. 42; Fungal Genetics and Biology; Elsevier Inc.

B.N. Chakraborty et al.; An electroporation-based system for high-efficiency transformation of germinated conidia of filamentous fungi; Journal; 1991; pp. 858-863, vol. 37; Can J Microbiol.
Xi Chen et al.; A fruiting body tissue method for efficient *Agrobacterium*-mediated transformation of *Agaricus bisporus*; Journal; Oct. 2000; pp. 4510-4513; vol. 66, No. 10; Applied and Environmental Microbiology; American Society for Microbiology.
Jean-Philippe Combier et al.; *Agrobacterium tumefaciens*-mediated transformation as a tool for insertional mutagenesis in the symbiotic ectomycorrhizal fungus *Hebeloma cylindrosporum*; Journal; 2003; pp. 141-148; vol. 220; FEMS Microbiology Letter; Elsevier Science B.V.
Marcel J.A. De Groot et al.; *Agrobacterium tumefaciens*-mediated transformation of filamentous fungi; Journal; Sep. 1998; pp. 839-842; vol. 16; Research; Nature Biotechnology; Nature Publishing Group.
T. Hirano et al.; Efficient transformation of the edible basidiomycete *Lentinus edodes* with a vector using a glyceraldehyde-3-phosphate dehydrogenase promoter to hygromycin B resistance.; 2000; Journal; vol. 263; pp. 1047-1052; Mol Gen Genet.; Springer-Verlag.
Toshikazu Irie et al.; Construction of a Homologous Selectable Marker Gene for *Lentinula edodes* Transformation; Journal; 2003; vol. 67, No. 9; pp. 2006-2009; Biosci Biotechnol Biochem.
Chun-Yi Kuo et al.; Cloning of glyceraldehyde-3-phosphate dehydrogenase gene and use of the gpd promoter for transformation in *Flammulina velutipes*; Journal; 2004; vol. 65, pp. 593-599; Appl Microbiol Biotechnol.

(Continued)

*Primary Examiner* — Kent L Bell
(74) *Attorney, Agent, or Firm* — WPAT, P.C.; Anthony King

(57) ABSTRACT

The invention develops a simple and reliable mushroom transformation procedure on the basis of electroporation of spores or mycelial fragments of mushroom.

10 Claims, 10 Drawing Sheets
(4 of 10 Drawing Sheet(s) Filed in Color)

OTHER PUBLICATIONS

Andreas Leclerque et al.; *Agrobacterium*-mediated insertional mutagenesis (AIM) of the entomopathogenic fungus *Beauveria bassiana*; Journal; 2004; vol. 45, pp. 111-119; Curr Genet.

Gang Li et al.; A highly efficient polyethylene glycol-mediated transformation method for mushrooms; Journal; 2006. vol. 256; pp. 203-208; FEMS Microbiol Letter; Federation of European Microbiological Societies; Blackwell Publishing Ltd.

Biao Ma et al.; The green fluorescent protein gene functions as a reporter of gene expression in *Phanerochaete chrysosporium*; Journal; Feb. 2001; vol. 67; pp. 948-955; Appl Environ Microbiol; American Society for Microbiology.

Thomas S.P. Mikosch et al.; Transformation of the cultivated mushroom *Agaricus bisporus* (Lange) using T-DNA from *Agrobacterium tumefaciens*; Journal; 2001; vol. 39, pp. 35-39; Curr Genet.; Springer-Verlag.

Luis G. Lugones et al.; Introns are necessary for mRNA accumulation in Schizophyllum commune; Journal; 1999; pp. 681-689; vol. 32, No. 4; Mol Microbiol.; Blackwell Science Ltd.

K. Ogawa et al.; Molecular breeding of the basidiomycete *Coprinus cinereus* strains with high lignin-decolorization and b-degradation activities using novel heterologous protein expression vectors; Journal; 1998; pp. 285-289; vol. 49; Appl Microbiol Biotechnol.; Springer-Verlag.

Toshitsugu Sato et al.; Transformation of the edible basidiomycete *Lentinus edodes* by restriction enzyme-mediated integration of plasmid DNA; Journal; 1998; pp. 2346-2350; vol. 62, No. 12; Biosci Biotechnol Biochem.

Miranda D. Van De Rhee et al.; Transformation of the cultivated mushroom, *Agaricus bisporus*, to hygromycin B resistance; Journal; 1996; pp. 252-258; vol. 250; Mol Gen Genet.; Springer-Verlag.

* cited by examiner (A)

(B)

METHOD FOR THE INTRODUCTION OF A HETEROLOGOUS POLYNUCLEOTIDE INTO A MUSHROOM

FIELD OF THE INVENTION

The invention relates to a method of introducing a heterologous polynucleotide into spores or mycelial fragments of mushroom that is based on an electroporation procedure.

BACKGROUND OF THE INVENTION

The practice of modern biotechnology relies upon a number of different genetic-engineering techniques in order to enable the expression of heterologous genes in various organisms. The application of biotechnology to cultivated mushrooms was initially hampered until certain experimental genetic-transformation systems had been developed. In consideration of molecular breeding and the potential of using mushrooms as expression hosts, researchers have put substantial effort into the development of genetic-transformation systems for edible mushrooms.

Researchers have attempted to develop a transformation system for commercial mushrooms, such as *A. bisporus*, for the introduction of novel characteristics. For other fungi, as well as plants, animals, and bacteria, the application of gene transfer technology is quite common and has already resulted in commercial application. However, the absence of an efficient, reproducible, stable transformation system generally applicable in a wild-type background in many fungi has strongly hampered molecular-biological research on such organisms.

In the past, most protocols used in fungal transformation involved electroporation of protoplasts (Chakraborty et al., 1991, Robinson and Sharon, 1999, van de Rhee et al., 1996), treatment of $CaCl_2$, polyethylene glycol (Ogawa et al., 1998, Sato et al., 1998), or restriction enzyme-mediated integration (Hirano et al., 2000, Irie et al., 2003, Sato et al., 1998). Only a few reports demonstrated the transformation of *L. edodes* (Hirano et al., 2000, Irie et al., 2003, Li et al., 2006, Sato et al., 1998). Since these transformation systems mainly relied on troublesome protoplast preparation, they were not applicable to other edible mushrooms which may not yield sufficient regenerable protoplasts and these transformation events might be inefficient or difficult to reproduce in other laboratories. *Agrobacterium tumefaciens*-mediated transformation has been routinely used for the genetic modification of a wide range of plant species and also demonstrated the ability to transfer DNA from a prokaryote to filamentous fungi (Chen et al., 2000, Combier et al., 2003, De Groot et al., 1998, Leclerque et al., 2004, Mikosch et al., 2001), nevertheless, this method is not necessarily appropriate for all mushroom species. Other fungi transformation schemes are disclosed in WO95/02691 and WO98/45455.

These have either had no success, or not been reproducible. Despite considerable interest in the development of a transformation scheme, no method is in general use today, due to low efficiency or lack of utility and convenience. Thus, there is a need to develop a highly effective and convenient genetic transformation system for mushroom.

SUMMARY OF THE INVENTION

One object of the invention is to provide a method of introducing a heterologous polynucleotide into a mushroom, comprising the steps of: a) constructing a plasmid having the heterologous polynucleotide; b) incubating mushroom spores for germination; c) harvesting the germinated spores and treating the spores with lysing enzymes; d) collecting the resulting spores and resuspending them in an electroporation buffer; e) mixing the spores suspended in the electroporation buffer with the plasmid; and f) subjecting the resulting mixture to electroporation wherein the electroporation is performed in electric resistance ranging from about 100 ohm to about 800 ohm and field strength ranging from 1.0 kV cm$^{-1}$ to 12.5 kV cm$^{-1}$.

Another object of the invention is to provide a method of introducing a heterologous polynucleotide into a mushroom, comprising the steps of: a) constructing a plasmid having the heterologous polynucleotide; b) collecting mycelial fragments of the mushroom and treating with lysing enzymes; c) suspending the mycelial fragments in an electroporation buffer; d)

mixing the mycelial fragments suspended in the electroporation buffer with the plasmid; and e) subjecting the resulting mixture to electroporation wherein the electroporation is performed in electric resistance ranging from about 100 ohm to about 800 ohm and field strength ranging from 1.0 kV cm$^{-1}$ to 12.5 kV cm$^{-1}$.

BRIEF DESCRIPTION OF THE DRAWING

The patent or application file contains at least one drawing executed in color. Copies of this patent or patent application publication with color drawing(s) will be provided by the Office upon request and payment of the necessary fee. The related drawings in connection with the detailed description of the present invention to be made later are described briefly as follows, in which.

CaMV35S polyA: CaMV35S (cauliflower mosaic virus 35S) polyA signal. Amp$^R$: the ampicillin resistance gene.

Figure 7:
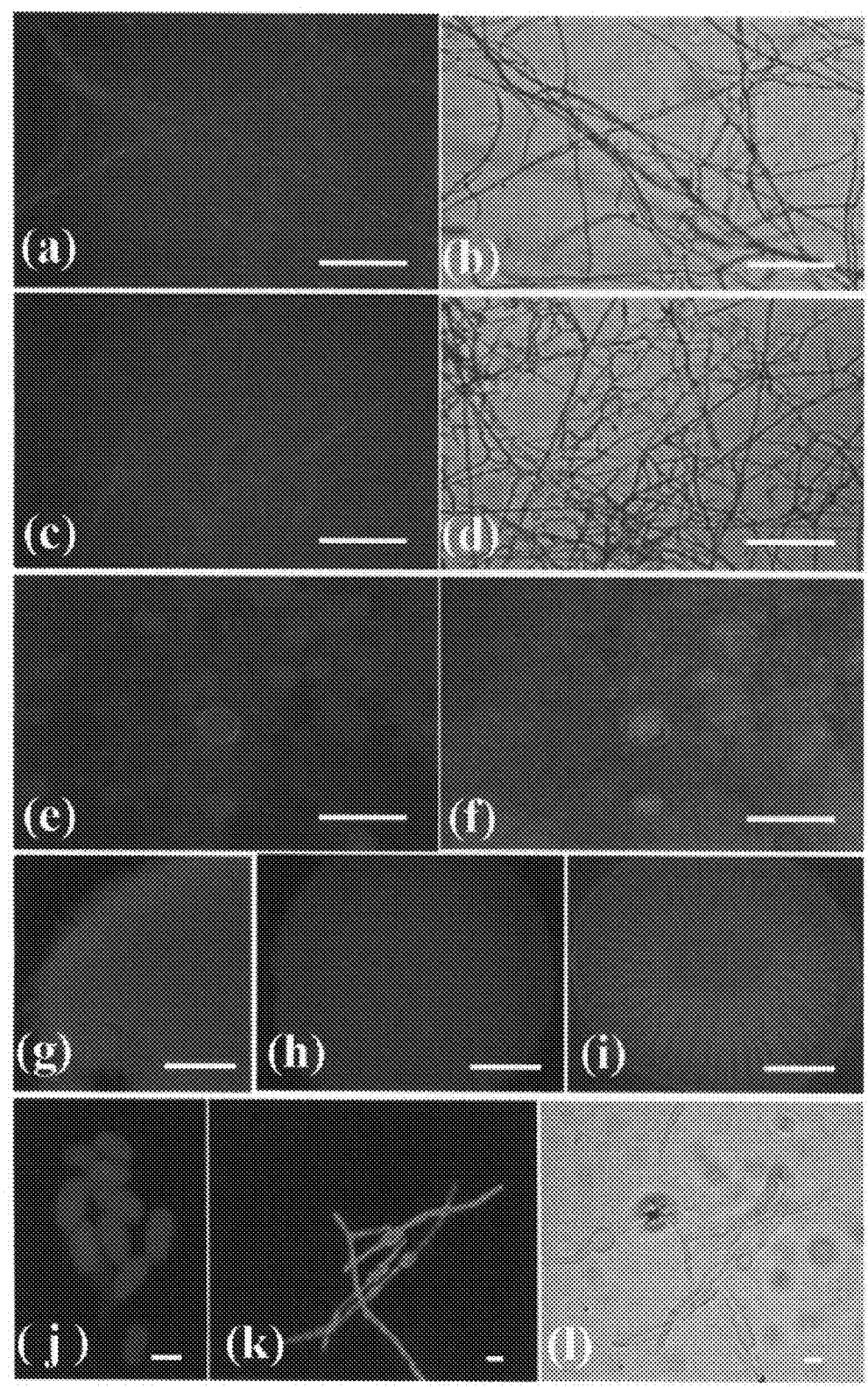

FIG. 7 shows expression of egfp in a *F. velutipes* transformant. Mycelia were collected from liquid-culture medium, suspended in sterile water, examined microscopically using a magnifying power of 400× (a-d) or directly detected from a colony cultured on a selection agar plate (e, f). Primordia (g) and mature fruiting bodies (h, i) were detected by a stereo fluorescence microscope. Isolated basidiospores collected prior to (j) and following germination (k, l) were also examined microscopically. (c, d and h): untransformed wild-type host strain. (a, c, e, g, h, i, j, k) were visualized using UV light; (b, d and l) by light microscopy, or both (f). Bar=10 m in (a-d); 40 m in (e and f); 0.5 mm in (g); 5 mm in (h and i); 5 m in (j, k and l).

Figure 8:
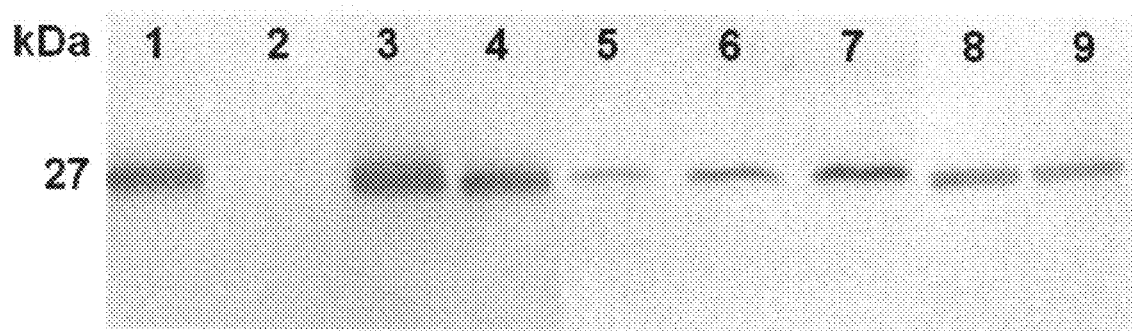

FIG. 8 shows western hybridization of EGFP of transformants. Lane 1: positive control of EGFP expressed in *E. coli*. Lane 2: negative control of total cellular protein from untransformed wild-type *F. velutipes*. Lane 3: total cellular protein from mycelia of transformant. Lane 4: water droplets collected from hyphae tip of transformant cultured on selective agar. Lane 5, 6, and 7: extracellular liquid culture supernatant of transformant as sampled on days 3, 7, and 10 respectively. Lane 8, 9: protein extracted from, respectively, cap and stem of mature fruiting body of transformant. Samples were fractionated using SDS-PAGE and blotted on a PVDF sequencing membrane. Detection was carried out with a (1:8,000) monoclonal anti-GFP living-colors peptide antibody.

Figure 9:
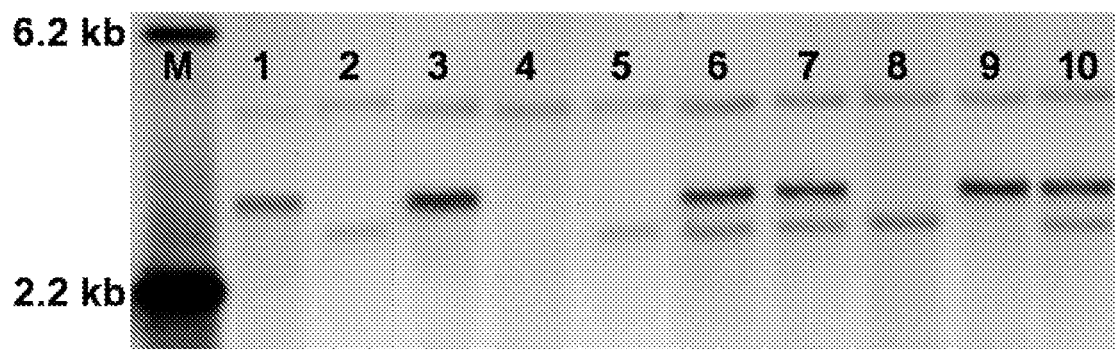

FIG. 9 shows southern-blot analysis of one dikaryon transformant and its nine green progeny. Lane 10: genomic DNA of dikaryon transformant; Lanes 1-9: Nine progeny from dikaryon transformant in Lane 10. SacI-digested genomic DNA was probed with the DIG-labeled egfp sequence. M, DNA molecular size markers (kilobases).

Figure 10:
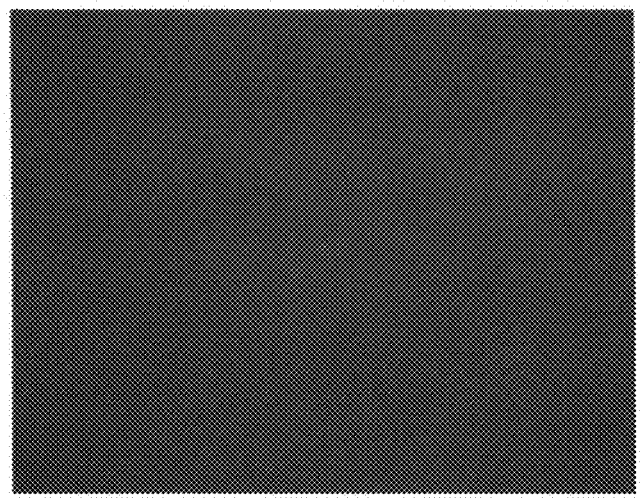
Figure 10:
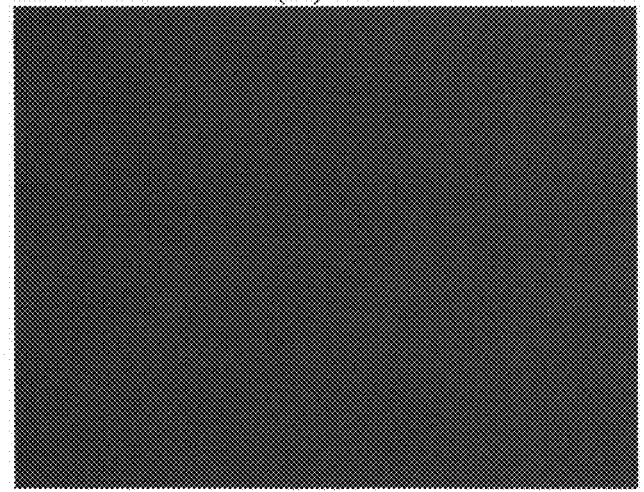

FIG. 10 shows the photos of the expression of EGFP in the transformant of *Pleurotus ostreatus* (FIG. 10(A)) and *Agaricus bisporus* (FIG. 10(B)).

DETAILED DESCRIPTION OF THE INVENTION

The invention develops a simple and reliable mushroom transformation procedure that is based on electroporation of spores or mycelial fragments of mushroom.

The invention provides a method of introducing a heterologous polynucleotide into a mushroom, comprising the steps of: a) constructing a plasmid having the heterologous polynucleotide; b) incubating mushroom spores for germination; c) harvesting the germinated spores and treating the spores with lysing enzymes; d) collecting the resulting spores and resuspending them in electroporation buffer; e) mixing the spores suspended in the electroporation buffer with the plasmid; and f) subjecting the resulting mixture to electroporation wherein the electroporation is performed in electric resistance ranging from about 100 ohm to about 800 ohm and field strength ranging from 1.0 kV cm$^{-1}$ to 12.5 kV cm$^{-1}$.

The invention also provides a method of introducing a heterologous polynucleotide into a mushroom, comprising the steps of: a) constructing a plasmid having the heterologous polynucleotide; b) collecting mycelial fragments and treating with lysing enzymes; c) suspending the mycelial fragments in an electroporation buffer; d) mixing the mycelial fragments suspended in the electroporation buffer with the plasmid; and e) subjecting the resulting mixture to electroporation wherein the electroporation is performed in electric resistance ranging from about 100 ohm to about 800 ohm and field strength ranging from 1.0 kV cm$^{-1}$ to 12.5 kV cm$^{-1}$.

According to the invention, the field strength used in the electroporation preferably ranges from 1.0 kV cm$^{-1}$ to 12.5 kV cm$^{-1}$ and the electric resistance preferably ranges from about 100 ohm to about 800 ohm. More preferably, the field strength ranges from 3 kV cm$^{-1}$ to 10 kV cm$^{-1}$, 5 kV cm$^{-1}$ to 10 kV cm$^{-1}$, 6 kV cm$^{-1}$ to 10 kV cm$^{-1}$ or 5 kV cm$^{-1}$ to 9 kV cm$^{-1}$ and the electric resistance preferably ranges from 200 ohm to 600 ohm, 200 ohm to 800 ohm or 500 ohm to 800 ohm. Most preferably, the electroporation is performed in electric resistance of 800 ohm and field strength of 5 kV cm$^{-1}$.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides.

A "heterologous" component refers to a component that is introduced into or produced within a different entity from that in which it is naturally located. For example, a polynucleotide derived from one organism and introduced by genetic engineering techniques into a different organism is a heterologous polynucleotide which, if expressed, can encode a heterologous polypeptide.

A "plasmid" refers to an extrachromosomal DNA molecule separate from the chromosomal DNA and capable of autonomous replication. The choice of plasmid is dependent upon the method that will be used to transform host cells. A skilled artisan is well aware of the genetic elements that must be present on the plasmid vector in order to successfully transform, select and propagate host cells containing the chimeric gene or chimeric construct. The skilled artisan will also recognize that different independent transformation events will result in different levels and patterns of expression.

An "electroporation" refers to a process involving the formation of pores in the cell membranes, or in any vesicles, by the application of electric field pulses across a liquid cell suspension containing the cells or vesicles.

According to the invention, a plasmid containing a heterologous polynucleotide is used as a donor for providing a genetic material. Any suitable heterologous polynucleotide can be used in the method of the invention. Preferably, the heterologus polynucleotide is a gene encoding an antibody, a secondary metabolite, a therapeutic compound, a biological macromolecule, or a medical enzyme; a gene that confer resistance to pests, diseases, or herbicides; or a gene that confers or contributes to a value-added trait.

According to the invention, spores or mycelial fragments of mushroom can be used as the receptacles for receiving the heterologous polynucleotide. Mushroom spores are incubated for germination. Preferably, they are incubated overnight with gentle shaking at room temperature (preferably about 25° C.). Mycelial fragments can be directly used in the method of the invention. Preferably, the mushroom is selected from the group consisting of *Lentinula, Flammulina, Agaricus, Hypsizygus*, and *Pleurotus*. More preferably, the mushroom is selected from the group consisting of *Lentinula edodes, Flammulina velutipes, Agaricus bisporus, Hypsizygus marmoreus*, and *Pleurotus ostreatus*.

The germinated spores or mycelial fragments are collected by any suitable method (for example, centrifugation and filtration) and resuspended in a buffer containing a lysing enzyme. The lysing enzyme is preferably zymolyase, lyticase, or lysing enzyme extracted from *Trichoderma harzianum* or *Rhizoctonia Solani*. More preferably, the lysing enzyme is Sigma L-1412. Preferably, the buffer is a phosphate buffer. After the treatment of the lysing enzyme, the spores or mycelial fragments are washed to remove the lysing enzyme and then resuspended in an electroporation buffer. According to the invention, the electroporation buffer may be electrolyte, non-electrolyte, or a mixture of electrolytes and non-electrolytes. Preferably, the electroporation buffer is HEPES buffer. More preferably, the electroporation buffer contains 1 mmol l$^{-1}$ HEPES, pH 7.5, 0.6 mol l$^{-1}$ mannitol. The plasmid having a heterologous polynucleotide is mixed with the resulting electroporation buffer and then an electroporation is performed. According to the invention, the electroporation is performed in electric resistance ranging from about 100 ohm to about 800 ohm and field strength ranging from 5 kV cm−1 to 12.5 kV cm−1.

During the electroporation process, cells are subjected to an electric field pulse and then suspended in a liquid medium. The length of the pulse (the time that the electric field is applied to a spore suspension) varies according to the spore type. To create a pore in a spore's wall and membrane, the electric field must be applied for a sufficient length of time and at the above specified voltage as to create a set potential across the cell membrane for a period of time long enough to create a pore.

The method of the invention is a simple and reproducible procedure based on germinated spores or mycelia electroporation successfully transformed a mushroom with higher efficiency and the heterologous gene expression. The mild pretreatment of germinated spores and mycelia fragments with lysing enzymes proved useful since it did not seriously compromise the integrity of the cell wall or the viability, while eliciting a marked enhancement in the yield of transformants. In one preferred embodiment of the invention, it was demonstrated that the heterologous gus gene could be expressed by gpd promoter with or without the first intron of gpd gene. When driven by gpd promoter with the intron, the average activity was 144.6±3.9 U mg$^{-1}$ soluble protein, almost five folds of the construction without the intron (30.1±0.7 U mg$^{-1}$). The results demonstrated that the electroporation procedure used in this study offers an efficient method for mushroom transformation without the troubling protoplast preparation. Since it does not require protoplast isolation and regeneration, the procedure is simple, reliable and reproducible. The method of the invention will benefit the mushroom biotechnology and related research.

EXAMPLE

Example 1

Expression of GUS in *Lentinula edodes*

Tested Strain

*Lentinula edodes* strain LD 106 was acquired from the culture collection of the Laboratory of Applied Microbiology, Institute of Microbiology and Biochemistry, National Taiwan University. Basidiomycetes were grown in either PDA (Potato dextrose agar, Difco, Detroit, Mich., USA) or PDB (Potato dextrose broth, Difco) at 25° C. Transformants were selected on PDA with 30 g ml$^{-1}$ Hygromycin (Sigma, St. Louis, Mo., USA). The *Escherichia coli* DH5 (GIBCOBRL, Life Technologies, Grand Island, N.Y., USA) was used for DNA manipulations and grown in LB medium (Sigma) at 37° C.

Plasmid Construction

Figure 1:
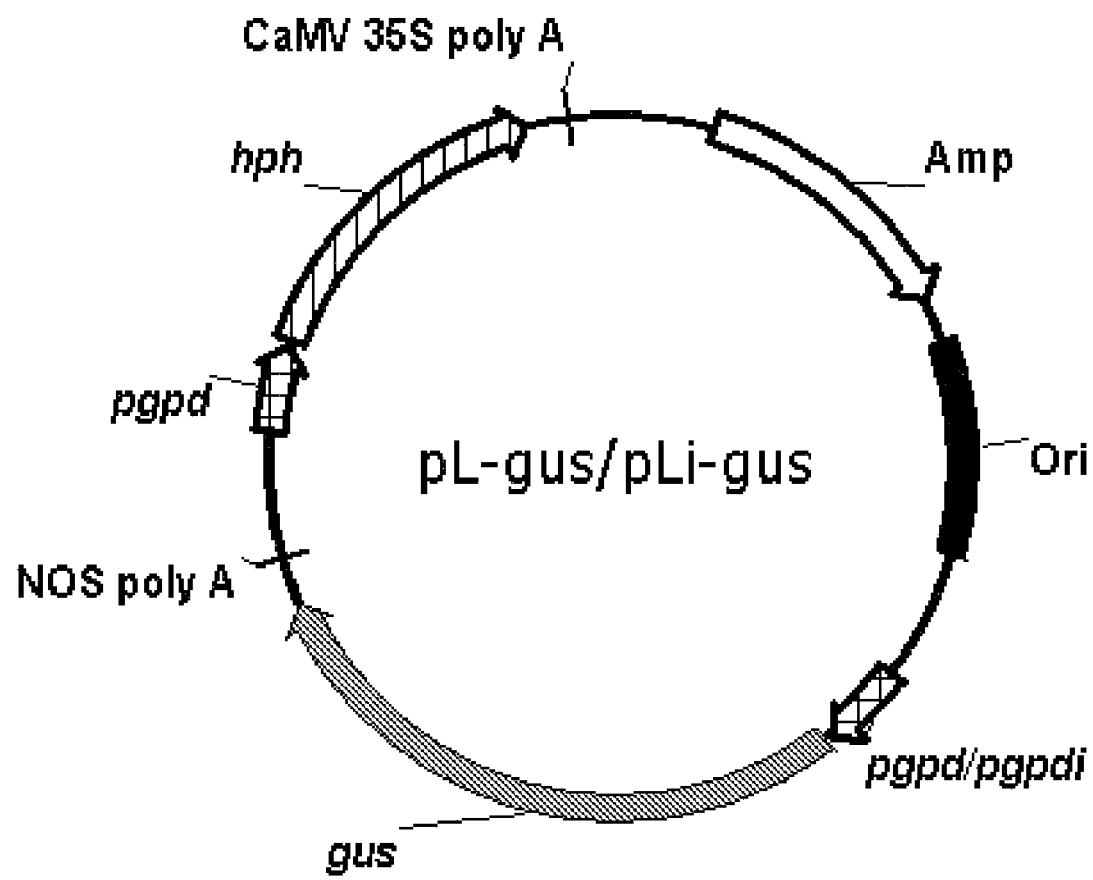
FIG. 1 shows the organization of pL-gus/pLi-gus for the expression of gus as reporter gene. The hygromycin-resistance gene (hph) was joined to the gpd promoter (pgpd), gus was driven with pgpd or pgpdi to produce pL-gus or pLi-gus. NOS poly A: nopaline synthase poly A signal. CaMV35S poly A: CaMV35S (cauliflower mosaic virus 35S) poly A signal. AmpR: the ampicillin resistance gene.

Two plasmids, pL-gus and pLi-gus, were constructed based on the backbone of plasmid pFGH (Kuo et al., 2004). Primers used to amplify promoter regions (pgpd) and reporter gene gus-Nos poly A are listed in Table 1. Reverse primer pL-ir and μL-r were used to amplify pgpd from *L. edodes* genomic DNA with (pgpdi) or without (pgpd) the first intron of gpd gene, respectively, while gus-Nos poly A was amplified from pCAMBIA 1391 (CAMBIA, Canberra, Australia). Hygromycin resistant gene (hph) was under control of pgpd without intron, but gus was driven with pgpd or pgpdi to produce pL-gus or pLi-gus. The schematic composition of the resultant plasmids used for the transformation experiments is illustrated in FIG. 1.

Transformation Procedure

Exponential-decay high voltage electric pulses were delivered by BTX ECM 630 and 0.2-cm cuvettes (BTX, San Diego, Calif.). The electric pulse delivery test conditions include several settings: capacitor 25 F; resistor from 100 ohm to 800 ohm and field strength from 6.25 kV cm$^{-1}$ to 12.5 kV cm$^{-1}$.

Basidiospores were collected from *L. edodes* fruiting bodies, suspended in PDB and incubated overnight with gentle shaking at 25° C. These germinated basidiospores were harvested by centrifugation at 2000 g for 5 min and resuspended in P buffer (0.02 mol l$^{-1}$ phosphate buffer, pH 5.8, 0.6 mol l$^{-1}$ mannitol) containing 2 mg ml$^{-1}$ lysing enzymes (Sigma). After incubation for 2 h, these basidiospores were washed free of enzyme and transferred to electroporation buffer (1 mmol l$^{-1}$ HEPES, pH 7.5, 0.6 mol l$^{-1}$ mannitol). About 10$^7$-10$^8$ basidiospores were mixed with 10 g plasmid DNA, chilled on ice for 10 min, and subjected to electroporation. After pulse delivery, basidiospores were kept on ice for 10 min and mixed with PDB containing 0.6 mol l$^{-1}$ mannitol. Transformants were selected on PDA plates containing 30 g ml$^{-1}$ hygromycin. The mycelium-based transformation procedure modified from the above technique was also developed. Four-day-old liquid cultures of *L. edodes* mycelia were blended in a Waring blender, and then incubated overnight with gentle shaking at 25° C. Mycelial fragments were collected by centrifugation at 3000 g and washed with P buffer. 300 l mycelium were mixed with 10 g plasmid DNA and the electroporation conditions described above were applied.

Detection and Stability of the Introduced Sequence in the Transformants

Genomic DNA isolated from putative hygromycin-resistant transformants was analyzed by PCR. Amplification of gus gene was carried out using primers Gus-f and Gus-r previously used in plasmid construction. The hph gene stability was assayed by transferring randomly selected transformants to a medium without antibiotic selection for weeks to months, and by a hygromycin-resistant test, followed.

Southern Hybridization

Approximately 5 g of genomic DNA digested by restriction enzymes was size-fractionated by electrophoresis on a 1% agarose gel. The DNA fragments in the agarose gel were transferred to a Hybond N$^+$ nylon membrane (Amersham, Hong Kong) using 10×SSC. The DNA fragments containing gus amplified by PCR from pCAMBIA 1391 were used as a probe for southern hybridization. Labeling of the DNA probe, hybridization, and signal detection were conducted by means of the Roche DIG-probe synthesis and detection kit (Roche, Mannheim, Germany) according to the manufacturer's instructions.

Detection of GUS in Transformants

For detection of β-glucuronidase activity, transformants were cultured in 10 ml PDB. After 10 days of incubation, the mycelia were washed with detection buffer (0.5% Triton X-100, 0.1 mol l$^{-1}$ sodium phosphate, pH 7.0) and incubated at 37° C. for 3 h in the detection buffer containing 0.5 mg ml$^{-1}$ X-gluc (5-Bromo-4-chloro-3-indolyl-D-Glucuronic Acid, Cycolhexylammonium Salt, Sigma). Microscopic observation was performed by an Olympus BH-2 Microscope (Tokyo, Japan). Assay for GUS activity was done by a β-glucuronidase fluorescent reporter gene activity detection kit (Sigma). Mycelium was frozen in liquid nitrogen and ground with a pestle. Protein extraction and activity determination were conducted according to the manufacturer's instructions. The fluorescence intensity of 4-MU was measured by the fluorometer FluoroMax-3 (Jobin Yvon and Glen Spectra, Edison, N.J.). One unit is defined as the amount of enzyme that releases one pmole of 4-MU from 4-MUG per minute at pH 7.0 and 37° C. Protein concentrations were determined by using a bicinchoninic acid assay (Pierce, Dallas, Tex.). The GUS expressed in $E.$ $coli$ by pET21a(+) served as a positive control enzyme.

Results

Transformation of $L.$ $edodes$

According to the procedures developed in our previous study (Kuo et al., 2004), the transformation efficiency using germinated basidiospores of $L.$ $edodes$ was about 50 transformants per g DNA. This method avoided protoplast preparation and the transformation efficiency was higher than other reports (Hirano et al., 2000, Irie et al., 2003, Sato et al., 1998). In contrast, the transformation efficiency using small mycelial fragments was about 30 transformants per g DNA. The growth rate and morphology showed no significant difference between transformants and the wild type strain.

Figure 2:
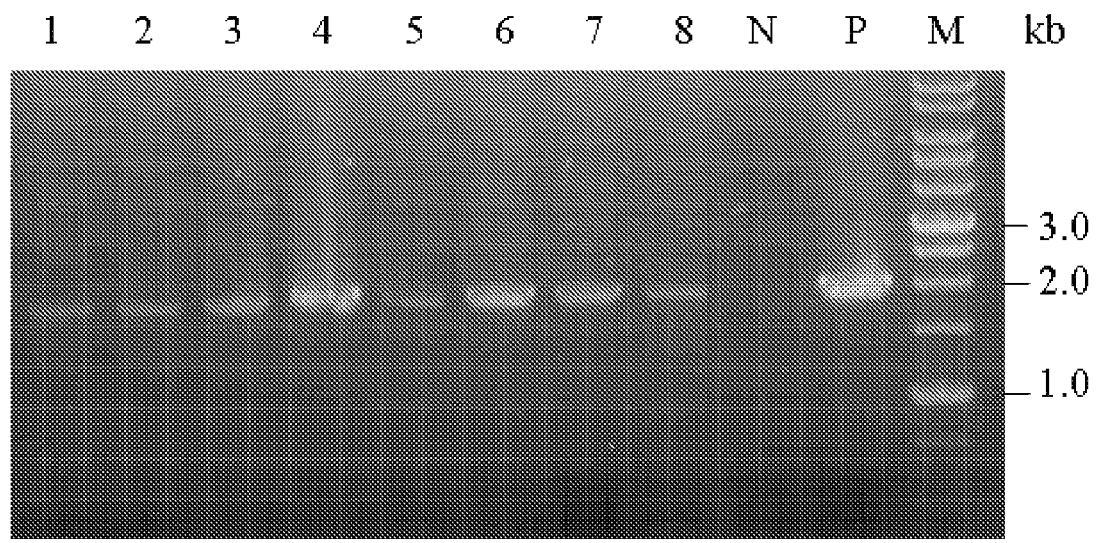
FIG. 2 shows the PCR analysis of DNA isolated from putative transformants. PCR amplification was carried out on genomic DNA using primers Gus-f and Gus-r defining a ~2.0 kb fragment containing gus gene and nopaline synthase poly A signal. Lanes: 1 to 8, DNA from randomly selected putative transformants; N, negative control with DNA isolated from nontransformed *L. edodes*; P, positive control with plasmid transformed.
Figure 3:
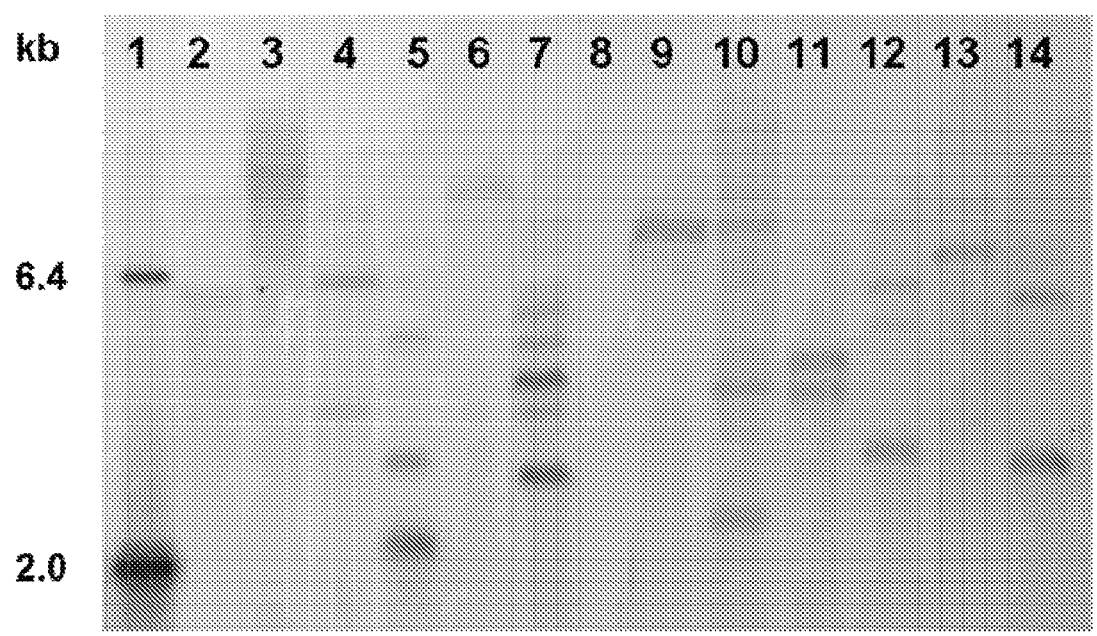
FIG. 3 shows the southern-blot analysis of the transformants. Lane 2-7, 9-14: Spe I-digested genomic DNA of transformants was probed with the DIG-labeled gus sequence. Lane 8: negative control of wild type genomic DNA. Lane 1: DNA molecular size markers (kilobases).

Subculturing transformants on media without selection pressure and then conducting a hygromycin-resistant test demonstrated that hygromycin resistance trait remained stable during mitotic cell division for at least six months. FIG. 2 shows the presence of gus DNA introduced via transformation checked by PCR amplification. No false positives were detected among 50 antibiotic-resistant cultures. In order to investigate the fate of transforming DNA, Southern hybridization was performed and the results are shown in FIG. 3. Southern hybridization analysis confirmed that multicopy integration of the heterologous genes occurred in the chromosomal DNA of tested transformants as evidenced by bands of various sizes. This result also suggested that the introduced fragment was integrated randomly into the genome.

Detection of GUS in Transformants

Figure 4:
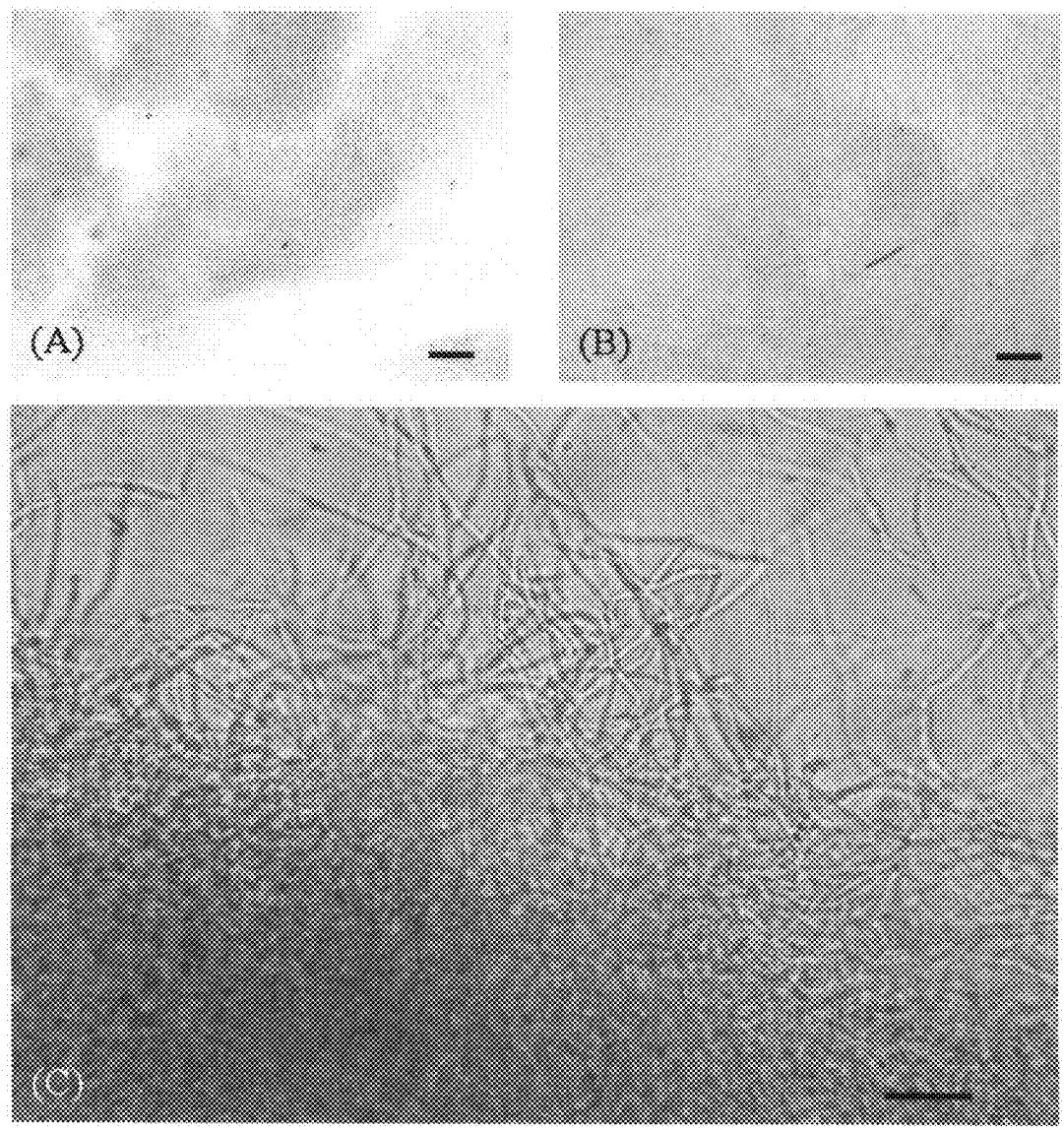
FIG. 4 shows the histochemical detection of GUS in *L. edodes*. Transformants were cultured in 10 mL PDB. After 10 days of incubation, the mycelia were washed in detection buffer and incubated at 37° C. for 3 h in detection buffer containing 0.5 mg mL$^{-1}$ X-gluc. (A), (C): transformants; (B) wild type. (A), (B): 40×, Bar=100 m; (C): 400×, Bar=10 m.

For histochemical detection of GUS in $L.$ $edodes$, the colonies that appeared on a selective medium were cultured in 10 ml PDB. After 10 days of incubation, the mycelia were collected for GUS detection. GUS activity was identified by formation of blue product from X-gluc (FIG. 4A, C), while the wild type host strain did not show blue color (FIG. 4B). Only 40~60% of $L.$ $edodes$ transformants showed GUS activity, though either pgpd or pgpdi could be used to drive gus gene expression. GUS expression remained stable through multiple rounds of subculturing without selection pressure for more than 6 months.

Activity Determination and Expression Level of GUS in $L.$ $edodes$

Figure 5:
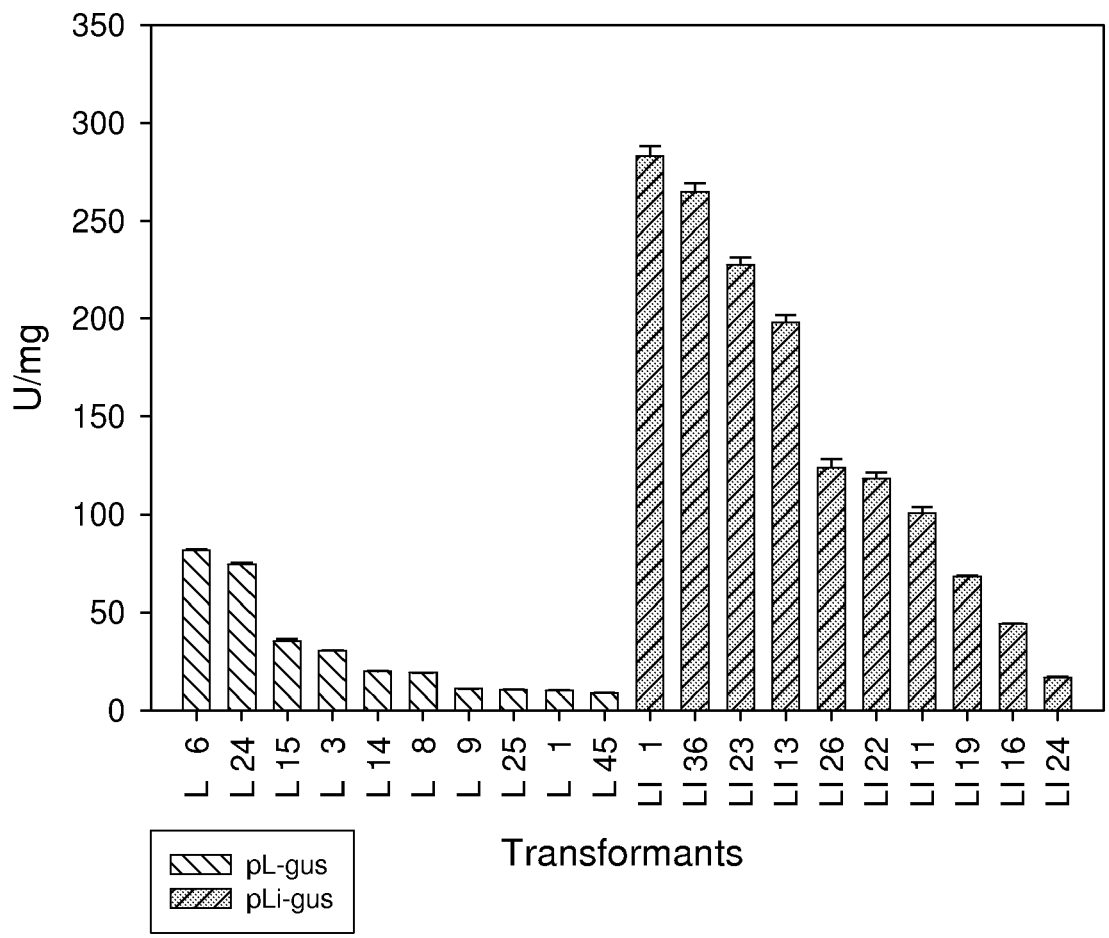
FIG. 5 shows the determination of GUS activities in transformants. GUS activities were present as unit per mg soluble protein extracted from mycelium. Top ten of transformants from both constructions were explained, error bars indicate standard deviations of three independent experiments.

Transformants confirmed by histochemical detection were chosen for GUS activity assay. Mycelia of thirty randomly selected transformants for gus driven by pgpd or pgpdi construction were washed free of medium, frozen and ground into fine powder, and then protein extraction occurred. FIG. 5 shows the GUS activities of the top ten transformants from each construction. When gus driven by pgpdi, containing the first intron of gpd gene, the average activity was 144.6±3.9 U $mg^{-1}$. In contrast, there were only 30.1±0.7 U $mg^{-1}$ on average for the transformants without the intron.

The purified GUS expressed from $E.$ $coli$ was used to determine the specific activity. The specific activity of purified GUS was $4.94 \times 10^5$ U $mg^{-1}$, i.e., 1 U of GUS activity was equivalent to 2 ng GUS protein. The highest GUS activity among the transformants was 283.3±4.91 U $mg^{-1}$ soluble protein, indicating that there were 566 ng GUS protein per mg soluble protein and the expression level was $5.66 \times 10^{-4}$ (0.06%).

Example 2

Expression of EGFP in $Flammulina$ $velutipes$

Strains and Media $Flammulina$ $velutipes$ BCRC 37086 was purchased from the Bioresources Collection and Research Center (Hsinchu, Taiwan) and cultured in either PDA (Potato dextrose agar, Difco, Detroit, Mich., USA) or PDB (Potato dextrose broth, Difco) at 25° C. Transformants were selected on PDA with hygromycin (30 g/ml). $Escherichia$ $coli$ DH5 (GIBCO-BRL, Life Technologies, Grand Island, N.Y., USA) was used for DNA manipulations and cultured in LB medium (Sigma Chem. Co., St. Louis, Mo., USA) at 37° C.

Fruiting Body Development of $F.$ $velutipes$

A medium composed of 65% sawdust and 35% rice bran was placed in a 500-ml flask and autoclaved for 1 h at 121° C. Such flasks were then sterilely inoculated with mycelial plugs and were incubated at 25° C. in the dark for three weeks. After vegetative mycelia grew throughout the medium, fruiting did not occur, and it was subsequently induced by the addition of sterile water, and a culture-temperature shift from 25° C. to 10° C. and the commencement of exposure of the culture to light. For primordia appearance and the maturation of developing fruiting bodies, the flasks were incubated at the same conditions until mature fruiting bodies appeared.

Plasmid Construction

Figure 6:
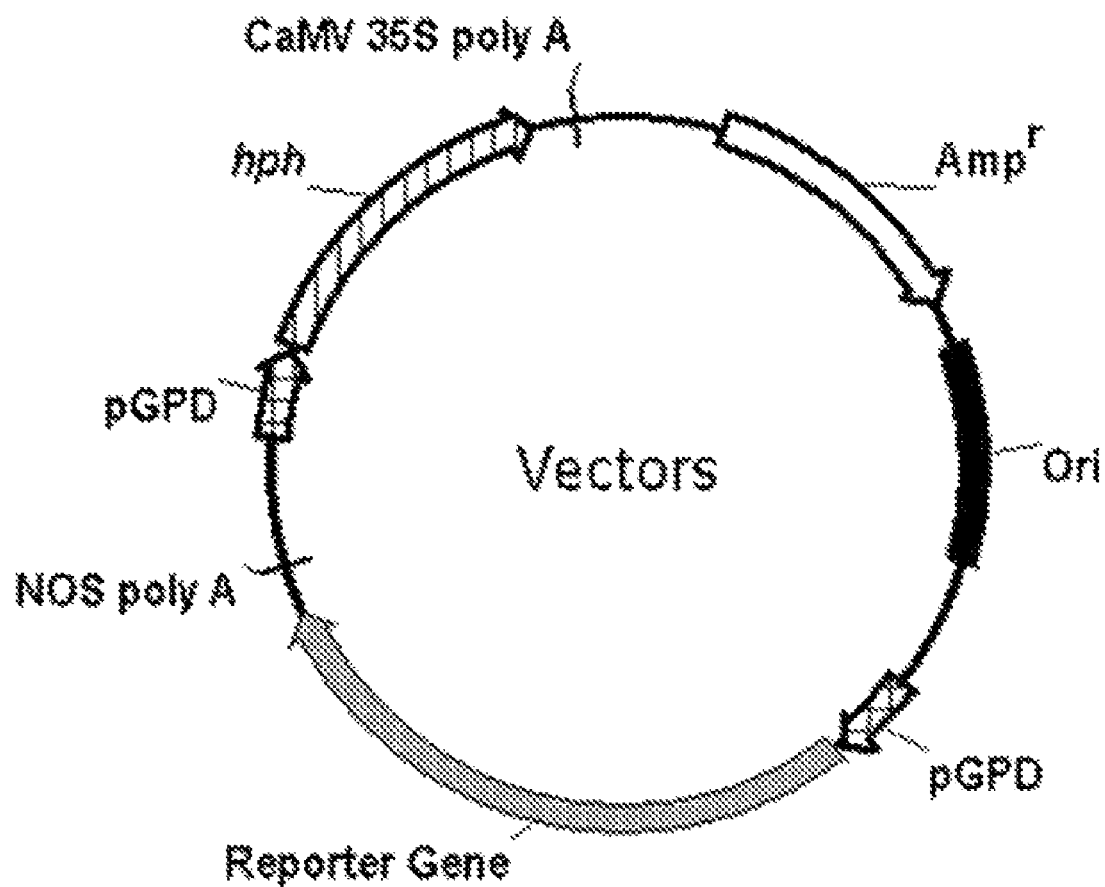
FIG. 6 shows organization of transformed plasmids for the expression of egfp as reporter gene. The hygromycin-resistance gene (hph) and egfp were joined to the gpd promoter (pGPD). NOS poly A: nopaline synthase poly A signal.

The plasmid pFGH was used as a backbone (Kuo et al., 2004). Appropriates primers were used to amplify reporter gene and egfp were amplified from pHygEGFP (BD Bioscience, Palo Alto, Calif., USA). The resulting plasmids (FIG. 6) were used for all study-reported transformation experiments.

Transformation Procedure

Transformation of $F.$ $velutipes$ was undertaken on the basis of a modification of the technique reported in a previous study (Kuo et al., 2004). Four-day-old liquid cultures of mycelia were blended using a Waring blender, and then incubated overnight with gentle shaking at 50 rpm at 25° C. Mycelial fragments were collected by centrifugation at 3,000 g for 5 mim, then washed with P buffer (0.02M phosphate buffer, pH=5.8, 0.6M mannitol) and treated with 2 mg/ml Lysing enzymes (Sigma) for 3 h. After washing the mycelial fragments free of enzyme, 0.5 g (wet weight), the fragments were mixed with plasmid DNA and subjected to electroporation. Electroporation was performed by BTX ECM 630 using 0.2-cm cuvettes (BTX, San Diego, Calif., USA) with an electric-pulse delivery setting of 25 F for the capacitor; 100 for the resistor and a 12.5 kV/cm setting for the field strength. Transformants were selected on PDA plates containing 30 g/ml hygromycin.

Detection of EGFP in Transformants

EGFP transformants were screened using a fluorescent microscope (E600, Nikon, Tokyo, Japan) fitted with a Nikon B-2A filter (450-490 nm excitation filter; 505 nm dichroic filter; 520 nm barrier filter). Fruiting bodies were observed using a stereo fluorescence microscope (SV11 APO/Axio-Cam MRc5, Carl Zeiss, Inc., Thornwood, N.J., USA).

Southern Hybridization

Genomic DNA isolation and southern hybridization procedures were conducted herein as was described previously (Kuo et al., 2004). Labeling of the DNA probe, hybridization, and signal detection were conducted by the Roche DIG-probe synthesis and detection kit (Roche, Mannheim, Germany) according to the manufacturer's instructions.

Western Hybridization

For western analysis of EGFP, *F. velutipes* transformants and the wild-type strain were cultured for seven days in PDB. Mycelia were collected and subsequently ground in liquid nitrogen using a mortar and pestle. A total of 50 mg mycelial powder was mixed with 1 ml protein-extraction buffer (50 mM sodium phosphate, pH=7.4, 1 mM PMSF, 0.1% Triton X-100, 0.5M NaCl) on ice for 5 min. Following centrifuging at 13,000 g for 20 min, supernatant was collected as total cellular protein. In order to verify the secretion of EGFP, the extracellular culture supernatant from the liquid culture and water droplets on the hyphae tip from the agar plate were collected and applied for immunoblotting. Total cellular protein and extracellular samples were separated by 10% sodium dodecyl sulfatepolyacrylamide gel electrophoresis (SDS-PAGE). The proteins were transferred to PVDF sequencing membrane (Millipore, Bedford, Mass., USA) using a semi-dry blotting system (Genmedika, Taipei, Taiwan). The detection of EGFP was carried out using a (1:8,000) monoclonal anti-GFP living-colors peptide antibody (BD Bioscience) and with the BCIP/NBT western detection kit (PerkinElmer, Boston, Mass., USA), using a procedure as described by the manufacturers.

Results

Transformation Procedure

Using the competent-cell preparation described in this study, small mycelial fragments, both dikaryons and monokaryons, were able to be transformed as easily as germinated basidiospores. The transformation efficiency was five to 20 transformants per g DNA while no hygromycin-resistant colonies were observed in the control experiment. As best we were able to determine, no significant difference in growth rate or morphology existed between transformants and the wild-type strain.

Detection of EGFP in Transformants

The presence of an intron for egfp expression in some basidiomycetes was reported previously (Burns et al., 2005; Lugones et al., 1999; Ma et al., 2001), therefore herein, the promoter region either with or without the first intron of the gpd gene was tested as a potential vehicle to drive egfp. About 30% of *F. velutipes* transformants prepared with the first intron exhibited green fluorescence (FIG. 7). The expression of egfp was able to remain stable following multiple rounds of subculture in the absence of any selection pressure. By contrast, no expression was observed in the construct prepared without the first intron region. Such results indicated that the presence of the 5' intron is required for egfp expression within *F. velutipes*.

The expression of egfp was also confirmed by western hybridization, as revealed in FIG. 8. Immunoblotting with the monoclonal anti-GFP antibody detected a 27-kDa polypeptide present in the positive control (Lane 1.) and also in the total cellular protein deriving from the transformant (Lane 3.), whereas no signal was detected in the untransformed strain (Lane 2.). By observing and identifying colonies on the selection agar plate using epifluorescent microscopy, water droplets emitting green fluorescence on the hyphae tip were able to be found (FIG. 7. *e, f*), whilst analogous water droplets from the wild type of *F. velutipes* did not show any fluorescence. In order to investigate the possibility of EGFP secretion from mycelia, the water droplets on the hyphae tip and the liquid culture sampled on days 3, 7, and 10 were independently examined by immunoblotting. The presence of extracellular EGFP was shown in Lanes 4-7 of FIG. 8, and these signals appeared to increase in intensity with time (Lanes 5-7, FIG. 8). These results in combination with the microscopic observations referred to above revealed that EGFP could be secreted extracellularly without the presence of secretion-signal peptide.

Using dikaryotic mycelial fragments as the recipient, ten randomly selected transformants that expressed egfp were inoculated into sawdust medium for fruiting-body isolation. Fruiting-body development was induced subsequent to vegetative mycelia growth all over the sawdust medium. Primordia appeared on the surface of sawdust three weeks subsequent to the induction of fruition. For the maturation of fruiting bodies, the sawdust medium-containing bottles were incubated at 10° C. and exposed to light for another 20 days. All of these transformants fructified successfully. Primordia and fruiting bodies were eventually collected for subsequent EGFP observation by fluorescent microscopy. Primordia produced less EGFP than mature fruiting bodies did, and intense green fluorescence was found to be distributed predominantly on the gills (FIG. 7.*g, i*). Although some autofluorescence was seen in the wild-type fruiting body when illuminated by UV light, there were obvious difference between transformed and non-transformed strains (FIG. 7.*h, i*). The presence of EGFP in fruiting bodies was also confirmed by immunoblotting (FIG. 8. Lanes 8, 9). Basidiospores isolated from these mushrooms revealed green fluorescence both before and after germination (FIG. 7.*j, k*), although not every basidiospore expressed egfp (FIG. 7.*k, l*). Southern analysis of one dikaryon and its nine monokaric green-fluorescent progeny, as illustrated in FIG. 9, revealed that the egfp became integrated into the genome of transformants and that all signals from the progeny coincided with those from the parental dikaryon. These results suggested that the integrated DNA remained stable during meiosis. To the best of our knowledge, this is the first report of egfp expression following meiosis in mushrooms in the relevant literature.

The expression level of EGFP in the transformant of Flammulina velutipes was determined by ELISA as stated in the quantification of EGFP by ELISA of Example 3. The quantified amount of EGFP from different transformants ranged from 10 to 23 mg EGFP per gram of total soluble protein. The percentage of EGFP in total soluble protein was $2 \times 10^{-2}$ (2%) in the transformant with the highest EGFP expression elvel.

Example 3

Expression of EGFP in *Pleurotus ostreatus*

Basidiospores were collected from *P. ostrestus* fruit bodies and suspended in PDB then incubated overnight with gentle shaking at 25° C. These germinated basidiospores were harvested by centrifugation at 2000 g for 5 min and resuspended in P buffer (0.02 M phosphate buffer, pH 5.8, 0.6 M mannitol) containing 3 mg/ml lysing enzymes (Sigma). After incubation for 2 h, these basidiospores were washed free of enzyme and transferred to a small volume of electroporation buffer (1 mM HEPES, pH 7.5, 0.6 M mannitol). Basidiospores ($10^7$-$10^8$) were mixed with 10 μg plasmid pPOH1 or pPOH2 containing egfp gene, chilled on ice for 10 min, and subjected to electroporation. Electroporation was performed by BTX ECM 630 using 0.2-cm cuvettes (BTX, San Diego, Calif., USA) with an electric-pulse delivery setting of 25 μF for the capacitor, 100Ω for the resistor and a 12.5 kV/cm setting for the field strength. Transformants were selected from PDA plates containing 30 μg/ml hygromycin.

Detection of EGFP in Transformants

EGFP transformants were screened by a fluorescent microscope (E600, Nikon, Tokyo, Japan) fitted with a Nikon B-2A filter (450-490 nm excitation filter; 505 nm dichroic filter; 520 nm barrier filter). FIG. 10(A) shows the photo of the expression of EGFP in the transformant of *Pleurotus ostreatus*.

Quantification of EGFP by ELISA

A sandwich ELISA for EGFP was conducted on 100 µl of each protein extract. Samples were incubated for 1 h on ELISA plates (PerkinElmer, Boston, Mass.) coated with monoclonal EGFP antibody (Abcam, Cambridge, UK). (Each sample was repeated in triplicate for each plate.) Rabbit anti-GFP polyclonal antibody (Abcam, Cambridge, UK) was added to each well at a 1:10,000 dilution and incubated for 1 h at 4° C. Goat polyclonal antibodies against rabbit IgG conjugated to HRP enzyme (PerkinElmer, Boston, Mass.) were added to each well at a 1:5,000 dilution and incubated for 1 h at 4° C. To each well, 100 µl of HRP substrate (BioFX, MD) was added. After 5 min, 50 µl of 1.0 M $H_2SO_4$ was added to stop the reaction. The absorbance at 450 nm was measured for each well using a 96-well plate reader (VERSAmax, Sunnyvale, Calif.). Protein concentrations were determined by using a bicinchoninic acid assay (Pierce, Dallas, Tex.). The EGFP expressed in *E. coli* by pET21a(+) serves as standards. A standard curve was calculated on the basis of the average values of the standards and used to estimate the amount of EGFP in the extract samples. The estimated EGFP values from ELISA method were reported as milligrams EGFP per gram total soluble protein.

The presence of an intron for egfp expression in some basidiomycetes was reported (Burns et al., 2005; Lugones et al., 1999; Ma et al., 2001). Therefore, herein, the promoter region with the first intron of the gpd gene was tested as a potential vehicle to drive egfp. About 80% of *P. ostreatus* transformants prepared with the first intron exhibited green fluorescence. The expression of egfp was able to remain stable after multiple rounds of subculture in the absence of any selection pressure. By contrast, no expression was observed in the construct prepared without the first intron region (data not shown). Such results indicated that the presence of the 5' intron is required for egfp expression within *P. ostreatus*.

The average amount of EGFP in the extract samples ranged from 0.4 to 5 mg per gram of total soluble protein from different transformants. The percentage of EGFP in total soluble protein was $5.4 \times 10^{-3}$ (0.5%) in the transformant with the highest EGFP expression level.

Example 4

Expression of EGFP in *Agaricus bisporus*

Liquid cultures of mycelia of *Agaricus bisporus* were blended using a Waring blender, and then incubated overnight with gentle shaking at 50 rpm at 25° C. Mycelial fragments were collected by centrifugation at 3,000 g for 5 mim, followed by washing with P buffer (0.02M phosphate buffer, pH=5.8, 0.6M mannitol) and treatment with 2 mg/ml Lysing enzymes (Sigma) for 3 h. After washing the mycelial fragments free of enzyme, 0.5 g (wet weight), the fragments were mixed with plasmid DNA containing egfp gene and subjected to electroporation. Electroporation was performed by BTX ECM 630 using 0.2-cm cuvettes (BTX, San Diego, Calif., USA) with an electric-pulse delivery setting of 25 F for the capacitor, 100 for the resistor and a 12.5 kV/cm setting for the field strength. Transformants were selected on PDA plates containing 30 g/ml hygromycin.

EGFP transformants were screened using a fluorescent microscope (E600, Nikon, Tokyo, Japan) fitted with a Nikon B-2A filter (450-490 nm excitation filter; 505 nm dichroic filter; 520 nm barrier filter). Fruiting bodies were observed using a stereo fluorescence microscope (SV11 APO/Axio-Cam MRc5, Carl Zeiss, Inc., Thornwood, N.J., USA). FIG. 10(B) shows the photo of the expression of EGFP in the transformant of *Agaricus bisporus*.

The expression level of EGFP in the transformant of *Agaricus bisporus* was determined by ELISA as stated in the quantification of EGFP by ELISA of Example 3. The quantified amount of EGFP from different transformants was up to 12.43±0.96 mg/g TSP. The percentages of EGFP in total soluble protein and mycelial dry weight were $1 \times 10^{-2}$ (1%) and $2 \times 10^{-3}$ (0.2%), respectively.

REFERENCES

1. Burns C, Gregory K E, Kirby M, Cheung M K, Riquelme M, Elliott T J, Challen M P, Bailey A, Foster G D (2005) Efficient GFP expression in the mushrooms *Agaricus bisporus* and *Coprinus cinereus* requires introns. Fungal Genet Biol 42: 191-199.
2. Chakraborty, B. N., Patterson, N. A., Kapoor, M., 1991. An electroporation-based system for high-efficiency transformation of germinated conidia of filamentous fungi. Can J Microbiol. 37, 858-863.
3. Chen, X., Stone, M., Schlagnhaufer, C., Romaine, C. P., 2000. A fruiting body tissue method for efficient *Agrobacterium*-mediated transformation of *Agaricus bisporus*. Appl Environ Microbiol. 66, 4510-4513.
4. Combier, J. P., Melayah, D., Raffier, C., Gay, G., Marmeisse, R., 2003. *Agrobacterium tumefaciens*-mediated transformation as a tool for insertional mutagenesis in the symbiotic ectomycorrhizal fungus *Hebeloma cylindrosporum*. FEMS Microbiol Lett. 220, 141-148.
5. De Groot, M. J., Bundock, P., Hooykaas, P. J., Beijersbergen, A. G., 1998. *Agrobacterium tumefaciens*-mediated transformation of filamentous fungi. Nat Biotechnol. 16, 839-842.
6. Hirano, T., Sato, T., Yaegashi, K., Enei, H., 2000. Efficient transformation of the edible basidiomycete *Lentinus edodes* with a vector using a glyceraldehyde-3-phosphate dehydrogenase promoter to hygromycin B resistance. Mol Gen Genet. 263, 1047-1052.
7. Irie, T., Sato, T., Saito, K., Honda, Y., Watanabe, T., Kuwahara, M., Enei, H., 2003. Construction of a Homologous Selectable Marker Gene for *Lentinula edodes* Transformation. Biosci Biotechnol Biochem. 67, 2006-2009.
8. Kuo, C. Y., Chou, S. Y., Huang, C. T., 2004. Cloning of glyceraldehyde-3-phosphate dehydrogenase gene and use of the gpd promoter for transformation in *Flammulina velutipes*. Appl Microbiol Biotechnol. 65, 593-599.
9. Leclerque, A., Wan, H., Abschutz, A., Chen, S., Mitina, G. V., Zimmermann, G., Schairer, H. U., 2004. *Agrobacterium*-mediated insertional mutagenesis (AIM) of the entomopathogenic fungus *Beauveria bassiana*. Curr Genet. 45, 111-119.
10. Li, G., Li, R., Liu, Q., Wang, Q., Chen, M., Li, B., 2006. A highly efficient polyethylene glycol-mediated transformation method for mushrooms. FEMS Microbiol Lett. 256, 203-208.
11. Ma B, Mayfield M B, Gold M H (2001) The green fluorescent protein gene functions as a reporter of gene expression in *Phanerochaete chrysosporium* Appl Environ Microbiol 67: 948-955.

12. Mikosch, T. S., Lavrijssen, B., Sonnenberg, A. S., van Griensven, L. J., 2001. Transformation of the cultivated mushroom *Agaricus bisporus* (Lange) using T-DNA from *Agrobacterium tumefaciens*. Curr Genet. 39, 35-39.
13. Lugones L G, Scholtmeijer K, Klootwijk R, Wessels J G (1999) Introns are necessary for mRNA accumulation in *Schizophyllum commune*. Mol Microbiol 32: 681-689.
14. Ogawa, K., Yamazaki, T., Hasebe, T., Kajiwara, S., Watanabe, A., Asada, Y., Shishido, K., 1998. Molecular breeding of the basidiomycete *Coprinus cinereus* strains with high lignin-decolorization and b-degradation activities using novel heterologous protein expression vectors. Appl Microbiol Biotechnol. 49, 285-289.
15. Sato, T., Yaegashi, K., Ishii, S., Hirano, T., Kajiwara, S., Shishido, K., Enei, H., 1998. Transformation of the edible basidiomycete *Lentinus edodes* by restriction enzyme-mediated integration of plasmid DNA. Biosci Biotechnol Biochem. 62, 2346-2350.
16. Van de Rhee, M. D., Graca, P. M., Huizing, H. J., Mooibroek, H., 1996. Transformation of the cultivated mushroom, *Agaricus bisporus*, to hygromycin B resistance. Mol Gen Genet. 250, 252-258.
17. WO95/02691.
18. WO98/45455.

What is claimed is:

1. A method of introducing a heterologous polynucleotide into a mushroom, comprising the steps of:
   a) constructing a plasmid having the heterologous polynucleotide;
   b) collecting mycelial fragments and treating the mycelial fragments with lysing enzymes, wherein no protoplast is produced;
   c) suspending the mycelial fragments in an electroporation buffer;
   d) mixing the mycelial fragments suspended in the electroporation buffer with the plasmid; and
   e) subjecting the resulting mixture to electroporation wherein the electroporation is performed in the electric resistance ranging from about 100 ohm to about 800 ohm and the field strength ranging from 1.0 kV cm$^{-1}$ to 12.5 kV cm$^{-1}$.

2. The method of claim 1, wherein the heterologous polynucleotide is a gene encoding an antibody, a secondary metabolite, a therapeutic compound, a biological macromolecule or a medical enzyme; a gene that confer resistance to pests, diseases, or herbicides; or a gene that confers or contributes to a value-added trait.

3. The method of claim 1, wherein the mycelial fragments are harvested or collected by filtration or centrifugation.

4. The method of claim 1, wherein the lysing enzyme is zymolyase, lyticase, or lysing enzyme extracted from *Trichoderma harzianum* or *Rhizoctonia Solani*.

5. The method of claim 1, wherein the mushroom is selected from the group consisting of *Lentinula, Flammulina, Agaricus, Hypsizygus*, and *Pleurotus*.

6. The method of claim 1, wherein the mushroom is selected from the group consisting of *Lentinula edodes, Flammulina velutipes, Agaricus bisporus, Hypsizygus marmoreus*, and *Pleurotus ostreatus*.

7. The method of claim 1, wherein the field strength used in the electroporation ranges from 3 kV cm$^{-1}$ to 10 kV cm$^{-1}$, 5 kV cm$^{-1}$ to 10 kV cm$^{-1}$, 6 kV cm$^{-1}$ to 10 kV cm$^{-1}$ or 5 kV cm$^{-1}$ to 9 kV cm$^{-1}$.

8. The method of claim 1, wherein the electric resistance ranges from 200 ohm to 600 ohm, 200 ohm to 800 ohm or 500 ohm to 800 ohm.

9. The method of claim 1, wherein the electroporation buffer is electrolyte, non-electrolyte or a mixture of electrolytes and non-electrolytes.

10. The method of claim 1, wherein the electroporation buffer is HEPES Buffer.

* * * * *